(12) United States Patent
Holub et al.

(10) Patent No.: US 9,492,575 B2
(45) Date of Patent: Nov. 15, 2016

(54) COLOR CHANGING AND DISINFECTING SURFACES

(71) Applicant: Ford Global Technologies, LLC, Dearborn, MI (US)

(72) Inventors: Patrick Kevin Holub, Novi, MI (US); John Robert Van Wiemeersch, Novi, MI (US); Stuart C. Salter, White Lake, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 14/735,435

(22) Filed: Jun. 10, 2015

(65) Prior Publication Data
US 2015/0273092 A1 Oct. 1, 2015

Related U.S. Application Data

(63) Continuation-in-part of application No. 14/603,636, filed on Jan. 23, 2015, which is a continuation-in-part of application No. 14/086,442, filed on Nov. 21, 2013.

(51) Int. Cl.
*B60Q 1/26* (2006.01)
*F21V 11/00* (2015.01)
*A61L 2/10* (2006.01)
(Continued)

(52) U.S. Cl.
CPC .. *A61L 2/10* (2013.01); *A61L 2/00* (2013.01); *A61L 9/00* (2013.01); *B60Q 3/008* (2013.01); *B60Q 3/0213* (2013.01); *B60Q 3/0293* (2013.01); *F21K 9/64* (2016.08); *H05B 37/0218* (2013.01); *H05B 37/0227* (2013.01); *F21Y 2105/10* (2016.08); *F21Y 2115/10* (2016.08); *Y02B 20/46* (2013.01)

(58) Field of Classification Search
CPC ............ A61L 2/10; A61L 9/00; A61L 2/00; F21K 9/64; B60Q 3/008; B60Q 3/0293; B60Q 3/0213; H05B 37/0227; H05B 37/0218; F21Y 2115/10; F21Y 2105/10; Y02B 20/46
See application file for complete search history.

(56) References Cited

U.S. PATENT DOCUMENTS

| | | |
|---|---|---|
| 5,709,453 A | 1/1998 | Krent et al. |
| 6,117,362 A | 9/2000 | Yen et al. |

(Continued)

FOREIGN PATENT DOCUMENTS

| | | |
|---|---|---|
| CN | 101337492 A | 1/2009 |
| CN | 201169230 Y | 2/2009 |

(Continued)

*Primary Examiner* — Donald Raleigh
(74) *Attorney, Agent, or Firm* — Vinchit Chea; Price Heneveld LLP

(57) ABSTRACT

An apparatus configured to disinfect a vehicle is disclosed. The apparatus comprises a first electrode substantially coating a portion of a partially light transmissive panel. A plurality of printed light emitting diodes (LEDs) is suspended in a semiconductor ink on the first electrode and configured to emit a disinfecting emission. A second electrode is in electrical connection with the plurality of LEDs. In connection with the second electrode and/or one or more intermediate layers a light transmitting layer is disposed forming an interior surface of the glass panel. The light transmitting layer is operable to transmit at least a portion of the disinfecting emission therethrough such that the portion of the disinfecting emission impinges upon an interior surface of the vehicle.

20 Claims, 7 Drawing Sheets

(51) Int. Cl.
    *B60Q 3/02*             (2006.01)
    *H05B 37/02*           (2006.01)
    *B60Q 3/00*             (2006.01)
    *A61L 2/00*             (2006.01)
    *A61L 9/00*             (2006.01)

(56) References Cited

U.S. PATENT DOCUMENTS

| | | | |
|---|---|---|---|
| 6,577,073 B2 | 6/2003 | Shimizu et al. |
| 6,729,738 B2 | 5/2004 | Fuwausa et al. |
| 6,737,964 B2 | 5/2004 | Samman et al. |
| 6,773,129 B2 | 8/2004 | Anderson, Jr. et al. |
| 6,820,888 B1 | 11/2004 | Griffin |
| 6,851,840 B2 | 2/2005 | Ramamurthy et al. |
| 6,859,148 B2 | 2/2005 | Miller |
| 6,871,986 B2 | 3/2005 | Yamanaka et al. |
| 6,953,536 B2 | 10/2005 | Yen et al. |
| 6,990,922 B2 | 1/2006 | Ichikawa et al. |
| 7,161,472 B2 | 1/2007 | Strumolo et al. |
| 7,213,923 B2 | 5/2007 | Liu et al. |
| 7,264,366 B2 | 9/2007 | Hulse |
| 7,264,367 B2 | 9/2007 | Hulse |
| 7,441,914 B2 | 10/2008 | Palmer et al. |
| 7,745,818 B2 | 6/2010 | Sofue et al. |
| 7,753,541 B2 | 7/2010 | Chen et al. |
| 7,834,548 B2 | 11/2010 | Jousse et al. |
| 7,862,220 B2 | 1/2011 | Cannon et al. |
| 7,987,030 B2 | 7/2011 | Flores et al. |
| 8,016,465 B2 | 9/2011 | Egerer et al. |
| 8,022,818 B2 | 9/2011 | La Tendresse et al. |
| 8,071,988 B2 | 12/2011 | Lee et al. |
| 8,097,843 B2 | 1/2012 | Agrawal et al. |
| 8,136,425 B2 | 3/2012 | Bostick |
| 8,163,201 B2 | 4/2012 | Agrawal et al. |
| 8,178,852 B2 | 5/2012 | Kingsley et al. |
| 8,197,105 B2 | 6/2012 | Yang |
| 8,203,260 B2 | 6/2012 | Li et al. |
| 8,207,511 B2 | 6/2012 | Bortz et al. |
| 8,232,533 B2 | 7/2012 | Kingsley et al. |
| 8,247,761 B1 | 8/2012 | Agrawal et al. |
| 8,286,378 B2 | 10/2012 | Martin et al. |
| 8,408,766 B2 | 4/2013 | Wilson et al. |
| 8,415,642 B2 | 4/2013 | Kingsley et al. |
| 8,421,811 B2 | 4/2013 | Odland et al. |
| 8,466,438 B2 | 6/2013 | Lambert et al. |
| 8,519,359 B2 | 8/2013 | Kingsley et al. |
| 8,519,362 B2 | 8/2013 | Labrot et al. |
| 8,552,848 B2 | 10/2013 | Rao et al. |
| 8,606,430 B2 | 12/2013 | Seder et al. |
| 8,624,716 B2 | 1/2014 | Englander |
| 8,631,598 B2 | 1/2014 | Li et al. |
| 8,664,624 B2 | 3/2014 | Kingsley et al. |
| 8,683,722 B1 | 4/2014 | Cowan |
| 8,724,054 B2 | 5/2014 | Jones |
| 8,773,012 B2 | 7/2014 | Ryu et al. |
| 8,846,184 B2 | 9/2014 | Agrawal et al. |
| 8,952,341 B2 | 2/2015 | Kingsley et al. |
| 9,057,021 B2 | 6/2015 | Kingsley et al. |
| 9,065,447 B2 | 6/2015 | Buttolo et al. |
| 9,299,887 B2 | 3/2016 | Lowenthal et al. |
| 2002/0159741 A1 | 10/2002 | Graves et al. |
| 2002/0163792 A1 | 11/2002 | Formoso |
| 2003/0179548 A1 | 9/2003 | Becker et al. |
| 2004/0213088 A1 | 10/2004 | Fuwausa |
| 2006/0087826 A1 | 4/2006 | Anderson et al. |
| 2006/0209551 A1 | 9/2006 | Schwenke et al. |
| 2007/0032319 A1 | 2/2007 | Tufte |
| 2007/0285938 A1 | 12/2007 | Palmer et al. |
| 2009/0219730 A1 | 9/2009 | Syfert et al. |
| 2009/0251920 A1 | 10/2009 | Kino et al. |
| 2009/0262515 A1 | 10/2009 | Lee et al. |
| 2011/0012062 A1 | 1/2011 | Agrawal et al. |
| 2012/0001406 A1 | 1/2012 | Paxton et al. |
| 2012/0020102 A1* | 1/2012 | Lambert ............ B60K 35/00 362/503 |
| 2012/0104954 A1 | 5/2012 | Huang |
| 2012/0183677 A1 | 7/2012 | Agrawal et al. |
| 2012/0280528 A1 | 11/2012 | Dellock et al. |
| 2013/0033894 A1* | 2/2013 | Kleo ............ B32B 17/10036 362/602 |
| 2013/0335994 A1 | 12/2013 | Mulder et al. |
| 2014/0065442 A1 | 3/2014 | Kingsley et al. |
| 2014/0098557 A1* | 4/2014 | Veerasamy ............ B60Q 1/268 362/545 |
| 2014/0103258 A1 | 4/2014 | Agrawal et al. |
| 2014/0240998 A1* | 8/2014 | Richard ............ B32B 17/10541 362/510 |
| 2014/0264396 A1 | 9/2014 | Lowenthal et al. |
| 2014/0266666 A1 | 9/2014 | Habibi |
| 2014/0373898 A1 | 12/2014 | Rogers et al. |
| 2015/0046027 A1 | 2/2015 | Sura et al. |
| 2015/0138789 A1 | 5/2015 | Singer et al. |
| 2015/0267881 A1 | 9/2015 | Salter et al. |
| 2016/0016506 A1 | 1/2016 | Collins et al. |

FOREIGN PATENT DOCUMENTS

| | | |
|---|---|---|
| CN | 201193011 Y | 2/2009 |
| CN | 201930271 U | 8/2011 |
| CN | 301655492 S | 8/2011 |
| CN | 102688510 A | 9/2012 |
| DE | 29708699 U1 | 7/1997 |
| DE | 10319396 A1 | 11/2004 |
| EP | 1793261 A1 | 6/2007 |
| EP | 2778209 A1 | 9/2014 |
| JP | 2000159011 A | 6/2000 |
| JP | 2007238063 A | 9/2007 |
| WO | 2006047306 A1 | 5/2006 |
| WO | 2014068440 A1 | 5/2014 |

* cited by examiner

US 9,492,575 B2

COLOR CHANGING AND DISINFECTING SURFACES

CROSS-REFERENCE TO RELATED APPLICATIONS

This application is a continuation-in-part of U.S. patent application Ser. No. 14/603,636, filed Jan. 23, 2015, and entitled "DOOR ILLUMINATION AND WARNING SYSTEM," which is a continuation-in-part of U.S. patent application Ser. No. 14/086,442, filed Nov. 21, 2013, and entitled "VEHICLE LIGHTING SYSTEM WITH PHOTOLUMINESCENT STRUCTURE." The aforementioned related applications are hereby incorporated by reference in their entirety.

FIELD OF THE INVENTION

The present disclosure generally relates to disinfecting systems, and more particularly, to disinfecting systems having thin profiles that may be operable to conform to non-planar surfaces.

BACKGROUND OF THE INVENTION

Disease and infection may be spread through indirect contact via various surfaces, which may correspond to touch surfaces that are commonly contacted. The disinfection of such surfaces may help prevent the spread of disease and infection to reduce associated health risks. The disclosure provides for various systems and apparatuses that may be utilized to disinfect various surfaces. At least one example of surfaces that may be disinfected by the disclosed apparatus may be various automotive vehicle surfaces.

SUMMARY OF THE INVENTION

According to one aspect of the present disclosure, an apparatus configured to disinfect a vehicle is disclosed. The apparatus comprises a first electrode substantially coating a portion of a partially light transmissive panel. A plurality of printed light emitting diodes (LEDs) is suspended in a semiconductor ink on the first electrode and configured to emit a disinfecting emission. A second electrode is in electrical connection with the plurality of LEDs. In connection with the second electrode and/or one or more intermediate layers, a light transmitting layer is disposed forming an interior surface of the glass panel. The light transmitting layer is operable to transmit at least a portion of the disinfecting emission therethrough such that the portion of the disinfecting emission impinges upon an interior surface of the vehicle.

According to another aspect of the present disclosure, a light emitting surface layer for a vehicle is disclosed. The surface layer comprises a pair of electrodes substantially coating a portion of a glass panel of the vehicle. A plurality of printed LEDs in a semiconductor ink is disposed between the electrodes and operable to emit an excitation emission of a first wavelength. A photoluminescent layer is disposed proximate one of the electrodes and configured to convert the excitation emission to an output emission of a second wavelength.

According to yet another aspect of the present disclosure, a light emitting assembly for a vehicle is disclosed. The assembly comprises a plurality of light generating layers or stacked emitting layers. Each of the light generating layers comprises a pair of electrodes substantially coating a portion of a glass panel of the vehicle and a plurality of printed LEDs. The plurality of printed LEDS is suspended in a semiconductor ink and disposed between the electrodes. The plurality of LEDs is operable to emit an excitation emission of a first wavelength. At least one of the light generating layers comprises a photoluminescent layer proximate one of the electrodes configured to convert the excitation emission to at least a first output emission of a second wavelength.

These and other aspects, objects, and features of the present disclosure will be understood and appreciated by those skilled in the art upon studying the following specification, claims, and appended drawings.

DETAILED DESCRIPTION OF THE PREFERRED EMBODIMENTS

As required, detailed embodiments of the present disclosure are disclosed herein. However, it is to be understood that the disclosed embodiments are merely exemplary of the disclosure that may be embodied in various and alternative forms. The figures are not necessarily to a detailed design and some schematics may be exaggerated or minimized to show function overview. Therefore, specific structural and functional details disclosed herein are not to be interpreted as limiting, but merely as a representative basis for teaching one skilled in the art to variously employ the present disclosure.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

In some embodiments, the following disclosure describes an illuminating and/or disinfecting apparatus for use with a fixture. The disinfecting apparatus may correspond to a surface layer or an emitting layer. The surface layer may be utilized for various surfaces that may be configured to emit a disinfecting emission to disinfect a region proximate the surface layer. The surfaces discussed herein may correspond to at least partially transparent surfaces. Such surfaces may include, but are not limited to at least partially light transmissive surfaces and may include a variety of surfaces that may be located proximate surfaces commonly contacted throughout their ordinary use.

The disinfecting apparatus may correspond to a thin, flexible assembly, which may be utilized in a variety of applications. For purposes of this disclosure, a vehicle fixture may refer to any interior or exterior piece of vehicle equipment, or part thereof, suitable for receiving various implementations of the apparatus described herein. In an exemplary embodiment, the vehicle fixture may correspond to a glass portion or window of the vehicle. While the various embodiments of apparatuses described herein are primarily directed to automotive vehicle use, it should be appreciated that the apparatus or system may also be implemented in other types of vehicles designed to transport one or more passengers such as, but not limited to, watercrafts, trains, and aircrafts.

Figure 1:
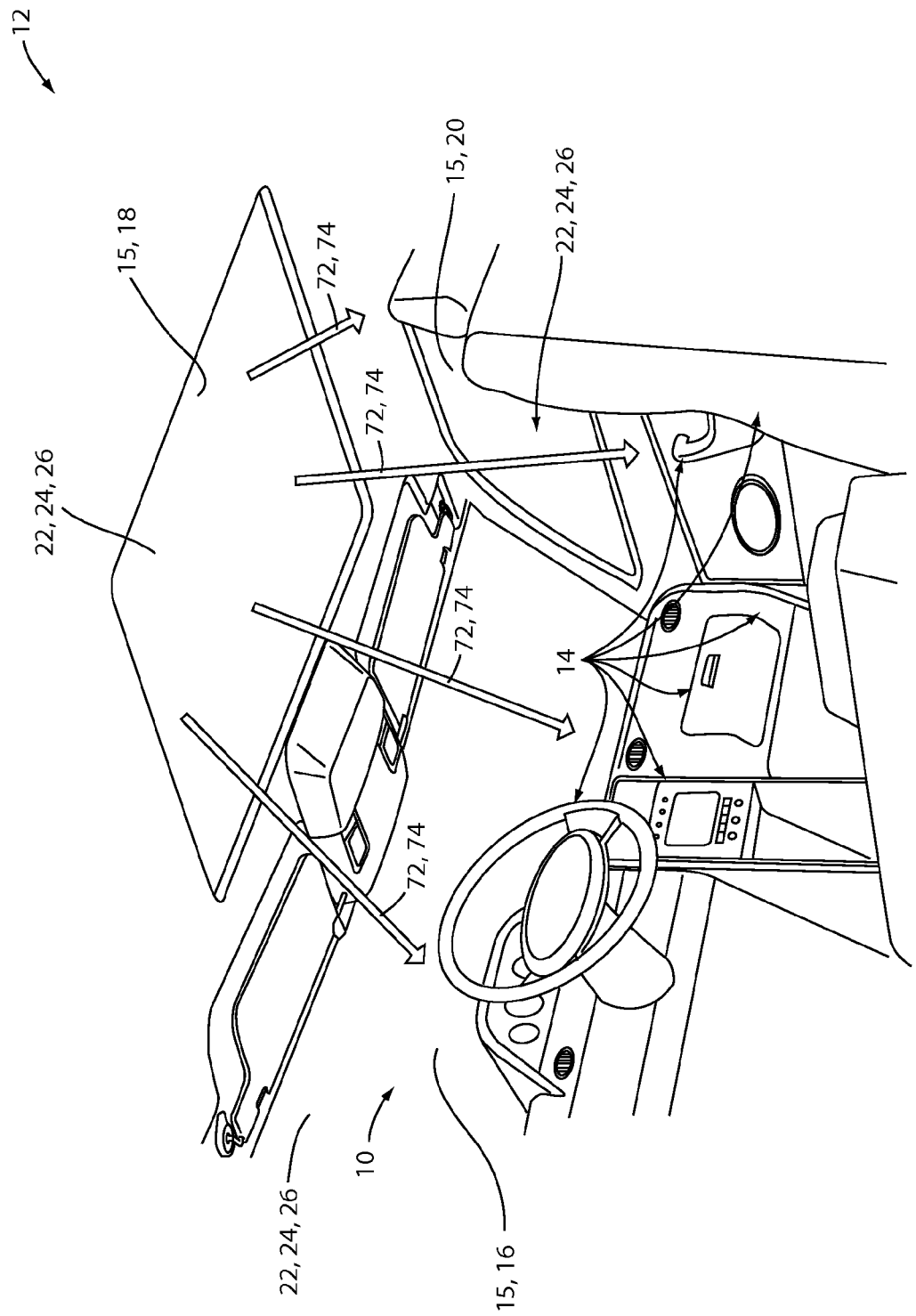
FIG. 1 is a perspective view of a passenger compartment of an automotive vehicle comprising a lighting assembly and/or surface layer.

Referring to FIG. 1, a passenger compartment 10 of an automotive vehicle 12 is generally shown demonstrating a variety of interior surfaces 14. During use and operation of the vehicle 12, the interior surfaces 14 may commonly be contacted by an operator, passenger, or otherwise such that bacteria and germs may accumulate on the interior surfaces 14. Such surfaces may include but are not limited to door handles, hand rails, arm rests, head rests, work surfaces (e.g. support surfaces), controls, seats, and a variety of additional fixtures and surfaces that may be contacted throughout ordinary use of the vehicle 12. The disclosure provides for a disinfecting apparatus 22 configured to emit an emission of light operable to disinfect at least a portion of the interior surfaces 14.

The disinfecting apparatus 22 may be disposed on a vehicle window 15 as a surface layer and/or as an integral layer of the vehicle window 15. The vehicle window, as discussed herein may correspond to any at least partially light transmissive portion of the vehicle 12 including but not limited to vehicle windows and portions thereof. In general, the vehicle windows 15 may correspond to a windshield 16, sun-roof 18, passenger window 20, and any other at least partially transparent or light transmissive panels or fixtures of the vehicle 12. The disclosure provides for at least one implementation of the disinfecting apparatus 22 disposed on a surface of the vehicle window 15 as a surface layer and/or as an integral layer of a vehicle window 15. The disinfecting apparatus 22 may be configured to output at least one wavelength of light configured to illuminate and/or disinfect a portion of the vehicle 12.

In some implementations, the disclosure further provides for an illumination apparatus 24 operable to illuminate at least a portion of the vehicle 12. The illumination apparatus 24 may be configured to adjust a color of an ambient light within the vehicle 12 by controlling a color of an emission of light output from the illumination apparatus 24. In some implementations, the illumination apparatus 24 may be implemented in combination with the disinfecting apparatus 22 as an integrated disinfection and lighting system, referred to hereinafter as the integrated lighting apparatus 26. In such embodiments, the integrated lighting apparatus 26 is operable to control a color of an ambient light in at least a portion of the vehicle 12 as well as provide for disinfection of the interior surface 14 of at least a portion of the vehicle 12.

In some embodiments, at least some of the apparatuses 22, 24, and 26 discussed herein may be in communication with a controller 172 (not shown). The controller 172 may further be in communication with a vehicle control module. The vehicle control module may provide signals to the controller 172 in response to various user inputs, vehicle operating information, vehicle status information, heating/cooling information, location information, occupant identity information, etc. In response to one or more signals received from the vehicle control module, each of the apparatuses 22 and 26 may be operable to output an emission of light, which may be configured to significantly disinfect at least a portion of an interior 10 of the vehicle 12. Additionally, an emission of visible light may be emitted from each of the apparatuses 24 and 26 and controlled by the controller 172 to correspond to various wavelengths of light and combinations thereof. Further details regarding the controller 172 and the vehicle control module are discussed in reference to FIG. 7.

Figure 2:
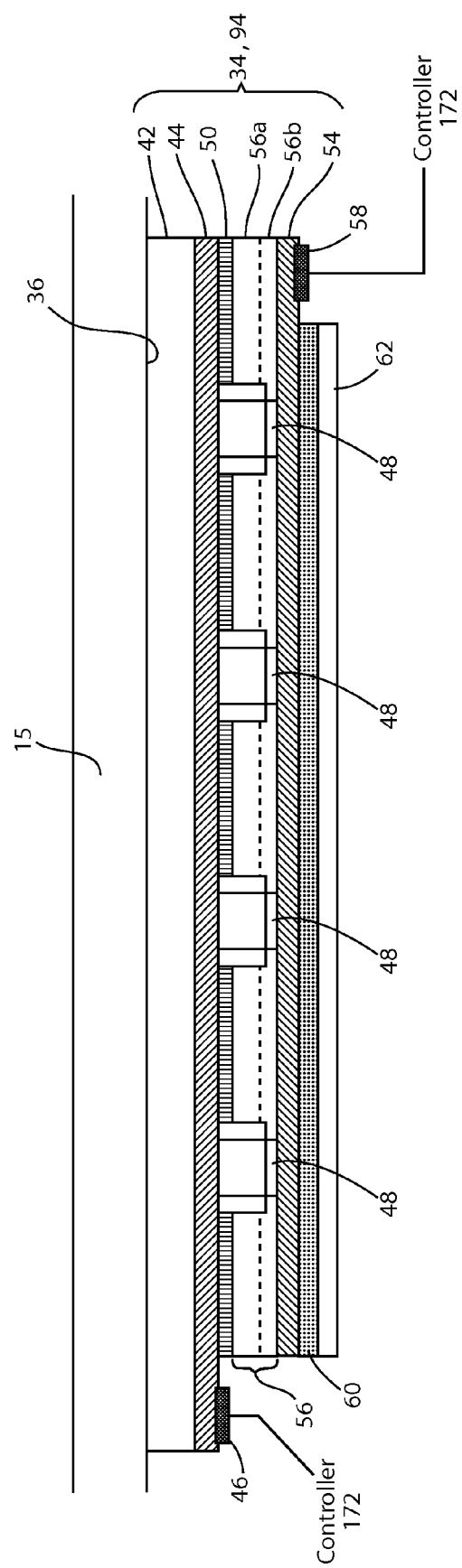
FIG. 2 is a detailed side view of a light producing assembly.

Referring to FIG. 2, a detailed side view illustrating an emitting layer 34 or light generating layer disposed on a glass surface 36, which may correspond to at least a portion of at least one of the apparatuses 22, 24, and 26, is shown. The emitting layer 34 may correspond to a thin-film or printed light-emitting diode (LED) assembly. For example, the emitting layer 34 may demonstrate a plurality of common features or elements that may be incorporated into each of the apparatuses 22, 24, and 26. Though each of the apparatuses 22, 24, and 26 may have particular combinations and/or configurations of the elements, the surface layers demonstrated in FIGS. 1 and 2 may provide exemplary configurations for each of the apparatuses 22, 24, and 26.

The emitting layer 34 is shown having a substrate 42 disposed on a glass surface 36 of vehicle window 15. The substrate 42 may be substantially transparent, or semi-transparent and may correspond to a thin film. The emitting layer 34 may be utilized in a variety of applications, which may require a thin overall thickness. The substrate 42 may be of a polymer, for example polycarbonate, poly-methyl methacrylate (PMMA), polyethylene terephthalate (PET), etc. In some embodiments, the substrate 42 may be dispensed from a roll to provide for integration into assembly operations for the emitting layer 34 and may be approximately 0.1 mm to 2 mm in thickness. In an exemplary implementation, the emitting layer 34 may be less than 1 mm in thickness and in some implementations, may be less than 0.6 mm in thickness.

A first electrode 44 may correspond to a cathodic conductive layer (hereinafter cathode 44) and may be disposed on the substrate 42. The cathode 44 and/or various electrodes or conductive layers discussed herein may comprise a conductive epoxy, such as a silver-containing or copper-containing epoxy. The cathode 44 is conductively connected to a first bus bar or a cathodic bus bar 46. The cathodic bus bar 46 and other bus bars or conduits discussed herein may be of metallic and/or conductive materials which may be screen printed on the electrodes or conductive layers. Bus bars may be utilized in the emitting layer 34 to conductively connect a plurality of light-emitting diode (LED) sources 48 to a power source via the controller 172. In this way, the cathodic bus bar 46, and other bus bars utilized in the emitting layer 34, may be configured to deliver electrical current substantially uniformly along and/or across the cathode 44 and other conductive layers in emitting layer 34.

The LED light sources 48 may be printed, dispersed or otherwise applied to the cathode 44 via a semiconductor ink 50. The semiconductor ink may correspond to a liquid suspension comprising a concentration of LED light sources 48 dispersed therein. The concentration of the LED light sources may vary based on a desired emission intensity of the light producing assembly. The LED light sources 48 may be dispersed in a random or controlled fashion within the semiconductor ink 50. The LED light sources 48 may correspond to micro-LEDs of gallium nitride elements, which may be approximately 5 microns to 400 microns in width substantially aligned perpendicular to the surface of the cathode 44. The semiconductor ink 50 may include various binding and dielectric materials including but not limited to one or more of gallium, indium, silicon carbide, phosphorous and/or translucent polymeric binders. In this configuration, the semiconductor ink 50 may contain various concentrations of LED light sources 48 such that a dispersion density of the LED light sources 48 may be adjusted for various applications.

The semiconductor ink 50 can be applied through various printing processes, including ink jet and silk screen processes to selected portion(s) of the cathode 44. The semiconductor ink 50 is applied such that the LED light sources 48 may form a circuit between the cathode 44 and a second electrode 54 or anodic conductive layer (hereinafter anode 54). More specifically, it is envisioned that the LED light sources 48 are dispersed within the semiconductor ink 50, and shaped and sized such that a substantial quantity of them preferentially align perpendicular to the cathode 44 and the anode 54 during deposition of the semiconductor ink 50. The portion of the LED light sources 48 that ultimately are electrically connected to the electrodes 44, 54 may be illuminated by a voltage source applied across the cathode 44 and the anode 54. Additional information regarding the construction of a light producing assembly similar to the emitting layer 34 is disclosed in U.S. Patent Publication No. 2014-0264396 A1 to Lowenthal et al., entitled "ULTRA-THIN PRINTED LED LAYER REMOVED FROM SUBSTRATE," filed Mar. 12, 2014, the entire disclosure of which is incorporated herein by reference.

At least one dielectric layer 56 may be printed over the LED light sources 48 to encapsulate and/or secure the LED light sources 48 in position. The at least one dielectric layer 56 may correspond to a first dielectric layer 56a and a second dielectric layer 56b, which may be of a transparent material. The anode 54 may correspond to a top transparent conductor layer printed over the dielectric layer 56 to electrically connect the electrodes 44, 54 via the LED sources 48. The anode 54 is conductively connected to a second bus bar or an anodic bus bar 58. The bus bars 46, 58 may be utilized in the emitting layer 34 to conductively connect a plurality of LED sources 48 to the power source via the controller 172.

The bus bars 46, 58 may be printed along opposite edges of the electrodes 44, 54 and electrically terminate at anode and cathode terminals. Points of connection between the bus bars 46, 58 and the controller 172 may be at opposite corners of each bus bar 46, 58 for uniform current distribution across the electrodes 44, 54. In an exemplary implementation, each of the electrodes 44, 54 may be of indium tin oxide (ITO) or similar conductive materials that are substantially light transmissive.

In operation, the LED light sources 48 may be configured to output an emission of light corresponding to a particular wavelength. The emission may be referred to as an excitation emission. The excitation emission may correspond to a various wavelengths of light. In an exemplary implementation, the LED light sources 48 excitation emission may correspond to a blue spectral, violet, and/or ultraviolet color range. The blue spectral color range comprises a range of wavelengths generally expressed as blue light (~440-500 nm). In some implementations, the first wavelength $\lambda_1$ may comprise a wavelength in the ultraviolet or near ultraviolet color range (~100-450 nm). In general, excitation emissions as discussed herein are utilized, at least in part, to activate or excite photoluminescent materials, which may be incorporated in the apparatuses discussed herein.

In some embodiments, an emission output from the LED light sources 48 may correspond to a variety of colors of light in the visible light range. For example, the LED light sources may be configured to emit red light (~620-750 nm), green light (~526-606 nm), blue light (~430-500 nm), and various combinations thereof. Additionally, the LED light sources 48 may be configured to emit various excitation emissions configured to excite photoluminescent materials to emit red light, green light, white light, and various colors of light. As discussed further in reference to FIGS. 4 and 5, the lighting apparatuses disclosed herein may be operable to selectively output emissions of various wavelengths in response to various signals received by the controller 172, which may correspond to various vehicle states operating conditions, etc..

Figure 3:
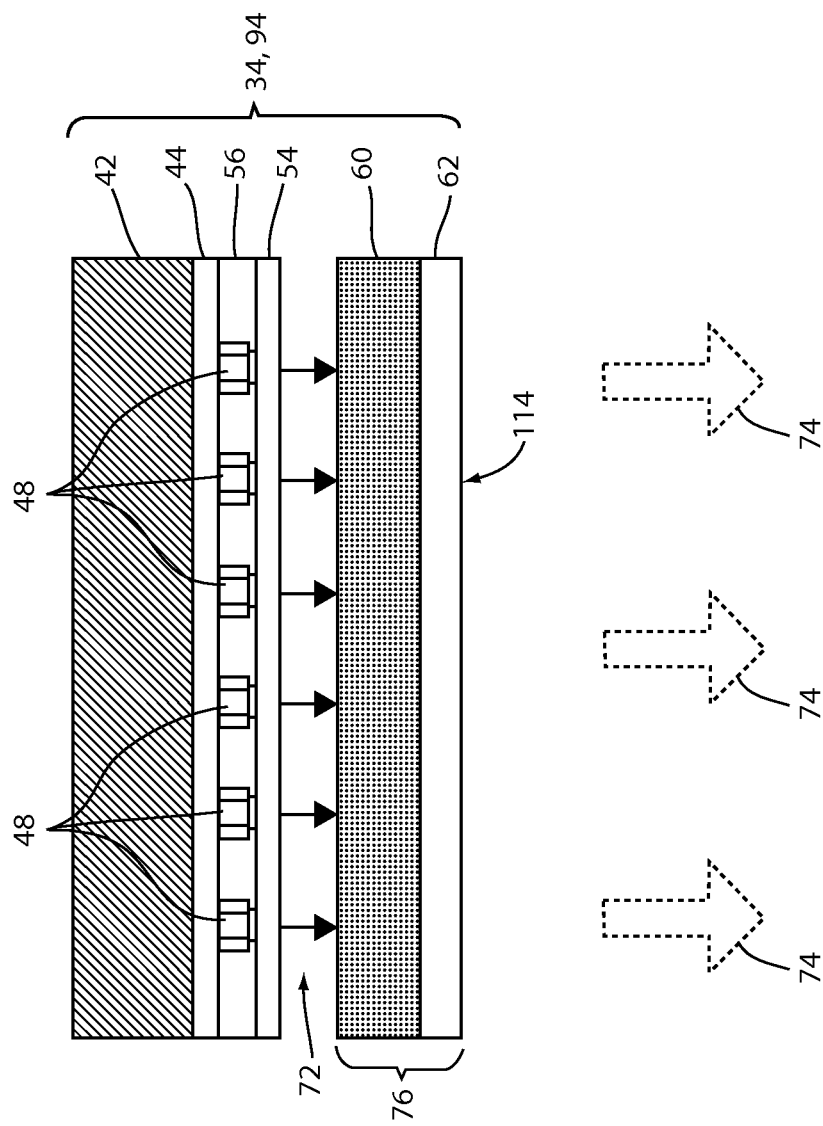
FIG. 3 is a side view of a light producing assembly demonstrating a photoluminescent layer configured to convert a wavelength of light.

Referring now to FIG. 2 and FIG. 3 in some implementations, a photoluminescent layer 60 may be applied to the anode 54. The photoluminescent layer 60 may be configured to convert at least a portion of an unconverted emission 72 or an excitation emission from the LED light sources 48 to an output emission 74 corresponding to light in the visible spectrum. The photoluminescent layer 60 may have a limited concentration of a photoluminescent material such that a first portion of the excitation emission or the unconverted emission 72 is converted to the output emission 74 and a second portion of the unconverted emission 72 is emitted from the emitting layer 34 as a disinfecting emission.

In this configuration, the output emission 74 may be emitted from an emitting surface 114 of the apparatus to illuminate at least a portion of the interior surface 14 of the vehicle 12 in a visible light while the second portion of the unconverted emission 72 may pass through the photoluminescent layer 60. The second portion of the unconverted emission 72 may be emitted from the emitting surface 114 as a disinfecting emission configured to disinfect at least a portion of one or more of the interior surfaces 14. As such, the emitting layer 34 may be operable to output an emission of light configured to illuminate and disinfect at least a portion of the vehicle 12.

The photoluminescent layer 60 may correspond to a coating, layer, film, and/or photoluminescent substrate. The photoluminescent layer 60 may be applied by screen printing, flexography, and/or otherwise affixed to the anode 54 or an intermediate layer therebetween. In various implementations, the LED light sources 48 may be configured to emit the unconverted emission 72 corresponding to ultraviolet (UV) light as a disinfecting emission. The LED light sources 48 may be configured to emit the unconverted emission 72 as an excitation emission into the photoluminescent layer 60 such that the photoluminescent material becomes excited. In response to the receipt of the unconverted emission 72, the photoluminescent material converts a portion of the unconverted emission 72 from the first wavelength to an output emission 74 comprising at least a second wavelength longer than the first wavelength.

The unconverted emission 72 may be emitted from the LED light sources 48, which may be configured to emit UV light. The LED light sources 48 may be configured to emit the unconverted emission 72 or excitation emission corresponding to a wavelength in the ultraviolet light range of approximately 10 nm to 400 nm. In an illustrative embodiment, the LED light sources 48 may be configured to emit ultraviolet radiation in the range of approximately 10 nm to 400 nm and in some embodiments may emit radiation at approximately 200 nm to 300 nm, which may be suited particularly for disinfection.

A light transmitting layer 62 or protective outer layer of the emitting layer 34 may correspond to one or more coatings. The light transmitting layer may be at least partially UV and visible light permeable. In some implementations, the light transmitting layer 62 or protective layer may correspond to a plurality of layers configured to provide a desired feel and appearance by projecting light into at least a portion of the vehicle 12. The light transmitting layer 62 may correspond to one or more coatings or sealing layers and may be applied to an exterior surface of the photoluminescent layer 60 or the anode 54. For example, the light transmitting layer 62 may be applied to the anode 54.

The light transmitting layer 62 maybe combined with the photoluminescent layer 60 for converting the first portion of the unconverted emission 72 to the output emission 74. In this configuration, the output emission 74 may be configured to illuminate at least a portion of the vehicle 12 in light corresponding to the visible spectrum of light. Additionally, a second portion of the unconverted emission 72 may be emitted from the light transmitting layer 62 corresponding to the UV spectrum of light. The second portion may be emitted into the vehicle 12 to disinfect at least a portion of the interior surfaces 14. The light transmitting layer 62 may correspond to an outer layer configured to protect the anode and/or the photoluminescent layer 60 and various other portions of the emitting layer 34 from damage and wear.

Referring now to FIG. 3, a detailed view of the photoluminescent layer 60 and the light transmitting layer 62 of the emitting layer 34 are shown. As discussed herein, the photoluminescent layer 60 may be utilized in some embodiments to convert at least a portion of the unconverted emission 72 to an output emission 74 in the visible light range. The LED light sources 48 are in electrical communication with the electrodes 44, 54 and a power source via the controller 172 such that the unconverted emission 72 may be output from LED light sources 48.

As previously discussed, in some implementations, the unconverted emission 72 output from the LED light sources 48 may correspond to a disinfecting emission having a first wavelength corresponding approximately to an ultra-violet spectral color range. The first wavelength may comprise a wavelength in the ultraviolet and near ultraviolet color range (~100-450 nm). In an exemplary implementation, the first wavelength may be approximately equal to 270 nm. Additionally, embodiments incorporating the photoluminescent layer, specific photoluminescent materials may be selected such that the photoluminescent layer 60 has an absorption range corresponding to the first wavelength. In this configuration, the photoluminescent material of the photoluminescent layer 60 may emit the output emission 74 in response to receiving the unconverted emission 72.

In embodiments that do not incorporate the photoluminescent layer 60, the unconverted emission 72 may pass directly into the light transmitting layer 62. In embodiments that incorporate the photoluminescent layer 60, the unconverted emission 72 is transmitted into an at least partially light transmissive material of the photoluminescent layer 60. The unconverted emission 72 is emitted from the LED light sources 48 and may be configured such that the first wavelength corresponds to at least one absorption range of one or more photoluminescent materials disposed in the photoluminescent layer 60. For example, the photoluminescent layer 60 may be configured to convert a portion of the unconverted emission 72 at the first wavelength to an output emission 74 having a second wavelength, different from the first wavelength. The photoluminescent layer may comprise a specific concentration of photoluminescent material to ensure that only a portion of the unconverted emission 72 is converted to the output emission 74. The output emission 74 may comprise one or more wavelengths, one of which may be longer than the first wavelength. The conversion of the unconverted emission 72 to the output emission 74 may be referred to as a Stokes shift.

In some embodiments, the output emission 74 may correspond to a plurality of wavelengths. Each of the plurality of wavelengths may correspond to significantly different spectral color ranges. For example, the at least second wavelength of the output emission 74 may correspond to a plurality of wavelengths (e.g. second, third, etc.). In some implementations, the plurality of wavelengths may be combined in the output emission 74 to appear as substantially white light. The plurality of wavelengths may be generated by a red-emitting photoluminescent material having a wavelength of approximately 620-750 nm, a green emitting photoluminescent material having a wavelength of approximately 526-606 nm, and a blue or blue green emitting photoluminescent material having a wavelength longer than the first wavelength $\lambda_1$ and approximately 430-525 nm. The plurality of wavelengths may be utilized to generate a wide variety of colors of light from the each of the photoluminescent portions converted from the first wavelength. Though the particular colors of red, green, and blue are referred to herein, various photoluminescent materials may be utilized to generate a wide variety of colors and combinations to control the appearance of the output emission 74.

The photoluminescent materials, corresponding to the photoluminescent layer 60 may comprise organic or inorganic fluorescent dyes configured to convert the unconverted emission 72 to the output emission 74. For example, the photoluminescent layer 60 may comprise a photoluminescent structure of rylenes, xanthenes, porphyrins, phthalocyanines, or other materials suited to a particular Stokes shift defined by an absorption range and an emission fluorescence. In some embodiments, the photoluminescent layer 60 may be of at least one inorganic luminescent material selected from the group of phosphors. The inorganic luminescent material may more particularly be from the group of Ce-doped garnets, such as YAG:Ce. As such, the photoluminescent portions may be selectively activated the first wavelength received from the unconverted emission 72 to emit an output emission 74 having a desired color.

Still referring to FIG. 3, the emitting layer 34 may further include the light transmitting layer 62 in the form of the at least partially light permeable layer. In some implementations, the light transmitting layer 62 may correspond to a plurality of layers configured to provide a desired appearance for a glass surface 36 of a window portion of the vehicle 12. The light transmitting layer 62 may correspond to one or more coatings or sealing layers and may be applied to a surface of the photoluminescent layer 60 or the anode 54. The light transmitting layer 62 may correspond to a protective outer layer and may comprise at least one stability layer configured to protect the photoluminescent material of the photoluminescent layer 60 from photolytic or thermal degradation and physical as well as chemical damage arising from environmental exposure. The stability layer may be configured as a separate layer optically coupled and adhered to the photoluminescent layer 60. The stability layer may also be integrated with the photoluminescent layer 60.

In some implementations, the light transmitting layer 62 may be integrated with the photoluminescent layer 60 and the stability layer to form an integrated photoluminescent structure 76 through sequential coating or printing of each layer, or by sequential lamination or embossing. Additionally, several layers may be combined by sequential coating, lamination, or embossing to form a substructure. The substructure may then be laminated or embossed to form the integrated photoluminescent structure 76. Once formed, the photoluminescent structure 76 may be applied to the anode 54 such that the unconverted emission 72 received from the LED light sources 48 is converted to the output emission 74. Additional information regarding the construction of photoluminescent structures to be utilized in at least one photoluminescent portion of a vehicle is disclosed in U.S. Pat. No. 8,232,533 to Kingsley et al., entitled "PHOTOLYTICALLY AND ENVIRONMENTALLY STABLE MULTI-LAYER STRUCTURE FOR HIGH EFFICIENCY ELECTROMAGNETIC ENERGY CONVERSION AND SUSTAINED SECONDARY EMISSION," filed Nov. 8, 2011, the entire disclosure of which is incorporated herein by reference.

Figure 4:
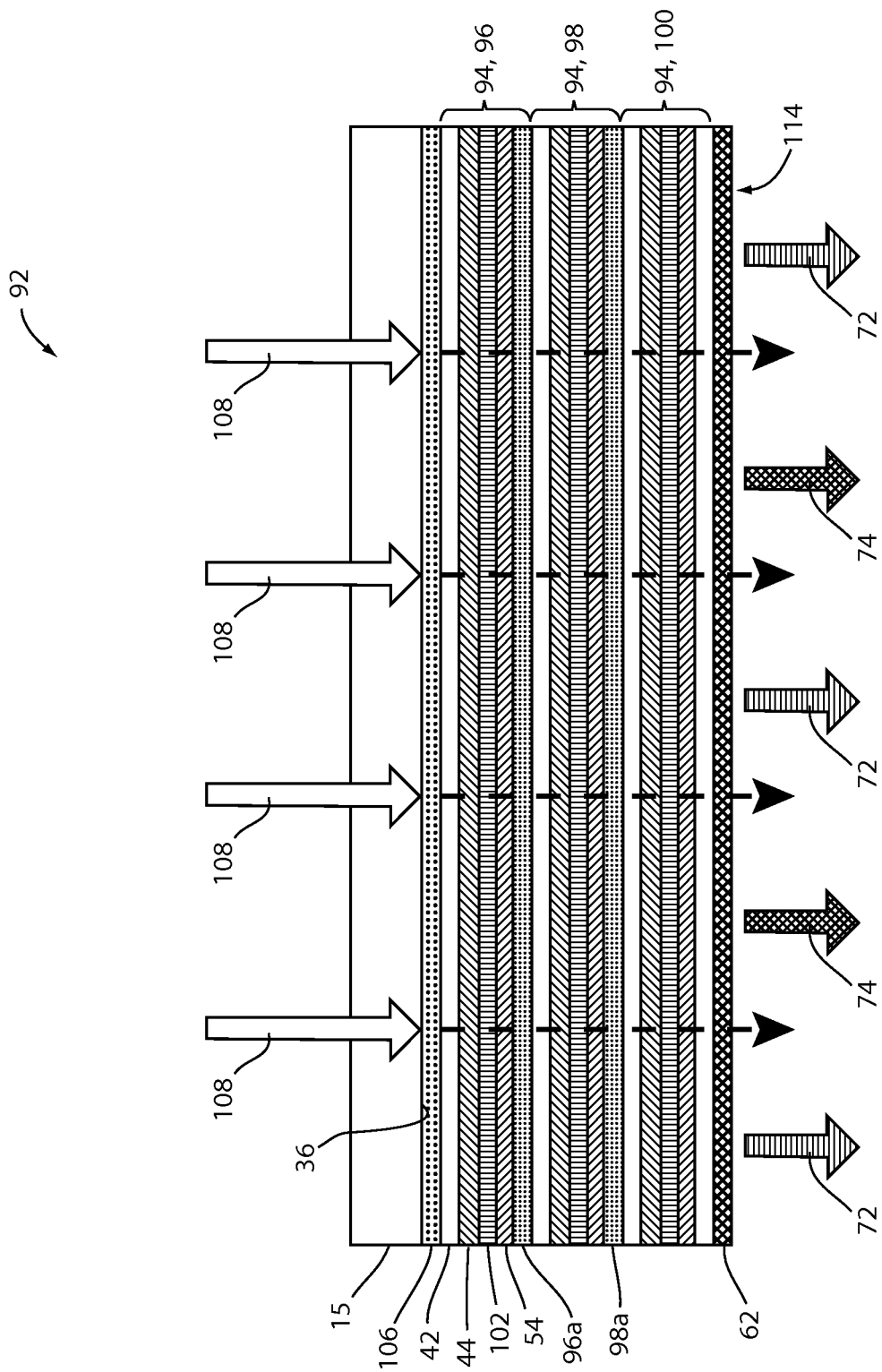
FIG. 4 is a detailed side view of an implementation of an at least semi-transparent color changing surface layer disposed on a glass surface of a vehicle.

Referring to FIG. 4, a detailed side view illustrating an implementation of a multi-layered lighting assembly 92 is shown disposed on the glass surface 36. The lighting assembly 92 may correspond to the apparatuses 24 and 26 and may be configured to emit the output emission 74 having a variety of wavelengths of light. For example, the lighting assembly 92 may be operable to emit the output emission 74 as red light, green light, blue light, ultraviolet light, and/or various combinations thereof. Each of a plurality of layers demonstrated in FIGS. 4 and 5 may correspond to structures similar to the emitting layer 34 discussed in reference to FIGS. 2 and 3 having like reference numerals. Specifically, in reference to FIG. 4, the layers form a plurality of stacked emitting layers 94 comprising a green emitting layer 96, a red emitting layer 98, and a blue emitting layer 100. The green emitting layer 96 and the red emitting layer 98 may comprise a green photoluminescent layer 96a and a red photoluminescent layer 98a, respectively. In this configuration, the controller 172 may independently activate a printed LED layer 102 of each of the layers 96, 98, and 100 to activate the output emission 74 to illuminate at least a portion of the vehicle 12 in a desired color.

The multi-layered lighting assembly 92 may correspond to the lighting apparatus 24 or the integrated apparatus 26 configured to generate the unconverted emission 72 and the output emission 74 in a plurality of wavelengths. The multi-layered lighting assembly 92 is shown laminated to or otherwise affixed to the glass surface 36 of a portion of window 15 of the vehicle 12. The lighting assembly may be affixed to the glass surface 36 by an adhesive 106, which may correspond to a substantially light transmissive adhesive or an optically clear adhesive. An example of an optically clear adhesive that may be utilized for the adhesive 106 may be an optically clear acrylic adhesive such as 3M™ Optically Clear Adhesives 8171 or 8172. In this way, the multi-layered lighting assembly 92 may be affixed to the glass surface 36 such that environmental light 108 outside the vehicle 12 may pass through the portion of the window 15 and into the multi-layered lighting assembly 92.

A mounting surface of the multi-layered lighting assembly 92 may correspond to the substrate 42 or a film layer. The substrate 42 may correspond to a layer of dielectric material configured to protect and electrically insulate a first stacked emitting layer, for example the green emitting layer 96. Each of the stacked emitting layers 94 may comprise the cathode 44 and the anode 54 with the printed LED layer 102 printed on a surface therebetween via a liquid suspension comprising a concentration of the LED light sources 48 dispersed therein. Additionally, each of the stacked emitting layers 94 may be separated by a substrate 42 in the form of a film layer or dielectric layer. In this configuration, the controller 172 in communication with each of the electrodes 44 and 54 of the respective stacked emitting layers 94 may selectively activate the printed LED layer 102 to generate the output emission 74 corresponding to the red light, green light, blue light, or any combination thereof from the respective stacked emitting layers 94.

As discussed herein, each of the stacked emitting layers 94 may be substantially transparent or at least partially light transmissible such that the environmental light 108 may pass through the multi-layered lighting assembly 92 and into the vehicle 12 in combination with the output emission 74. In this way, the stacked emitting layers 94 of the multi-layered lighting assembly 92 may be operable to illuminate the interior surface 14 of the vehicle 12 and also blend with the environmental light 108 transmitted through the portion of the window 15 and into the multi-layered lighting assembly 92. The various implementations discussed herein provide for a lighting apparatus operable to illuminate the interior surface 14 of the vehicle 12 with almost any color of light and also may be utilized to emit a disinfecting emission of UV light into the vehicle to disinfect at least a portion of the interior surface 14 of the vehicle 12.

As illustrated in FIG. 4, the stacked emitting layers 94 are arranged such that the green emitting layer 96 is closest to the glass surface 36, the blue emitting layer 100 is closest to the interior of the vehicle 12 or an emitting surface 114, and the red emitting layer 98 may be disposed therebetween. The emitting surface 114 may be configured to diffuse the unconverted emission 72 such that the colors corresponding to each of the emitting stacks 94 are emitted substantially uniformly from an emitting surface 114 of the light transmitting layer 62. In some implementations, the order of each of the emitting layers 96, 98, and 100 may vary. However, it may be noted that in some exemplary implementations, it may be beneficial to include the blue emitting layer 100 closest to the emitting surface 114.

As shown in FIG. 4, the printed LED layer 102 of each of the stacked emitting layers 94 may comprise LED light sources 48 configured to emit excitation emissions corresponding to substantially blue light having wavelengths of approximately 420 nm-500 nm. With the blue emitting layer 100 disposed closest to the emitting surface 114 in reference to the red, green, and blue emitting layers 96, 98, and 100, the blue light generated by the printed LED layer 102 of the blue emitting layer 100 may be output into the vehicle 12. In this configuration, the blue light may be output from the emitting surface to form at least a portion of the unconverted emission 72 without being converted to a different wavelength of light by the photoluminescent layers 60. This configuration may be particularly beneficial to some particular implementations of the lighting apparatuses discussed herein, but should not be considered to limit various combinations of LED light sources configured to emit different wavelengths of light to excite corresponding photoluminescent materials in each of the stacked emitting layers 94 as described herein.

Figure 5:
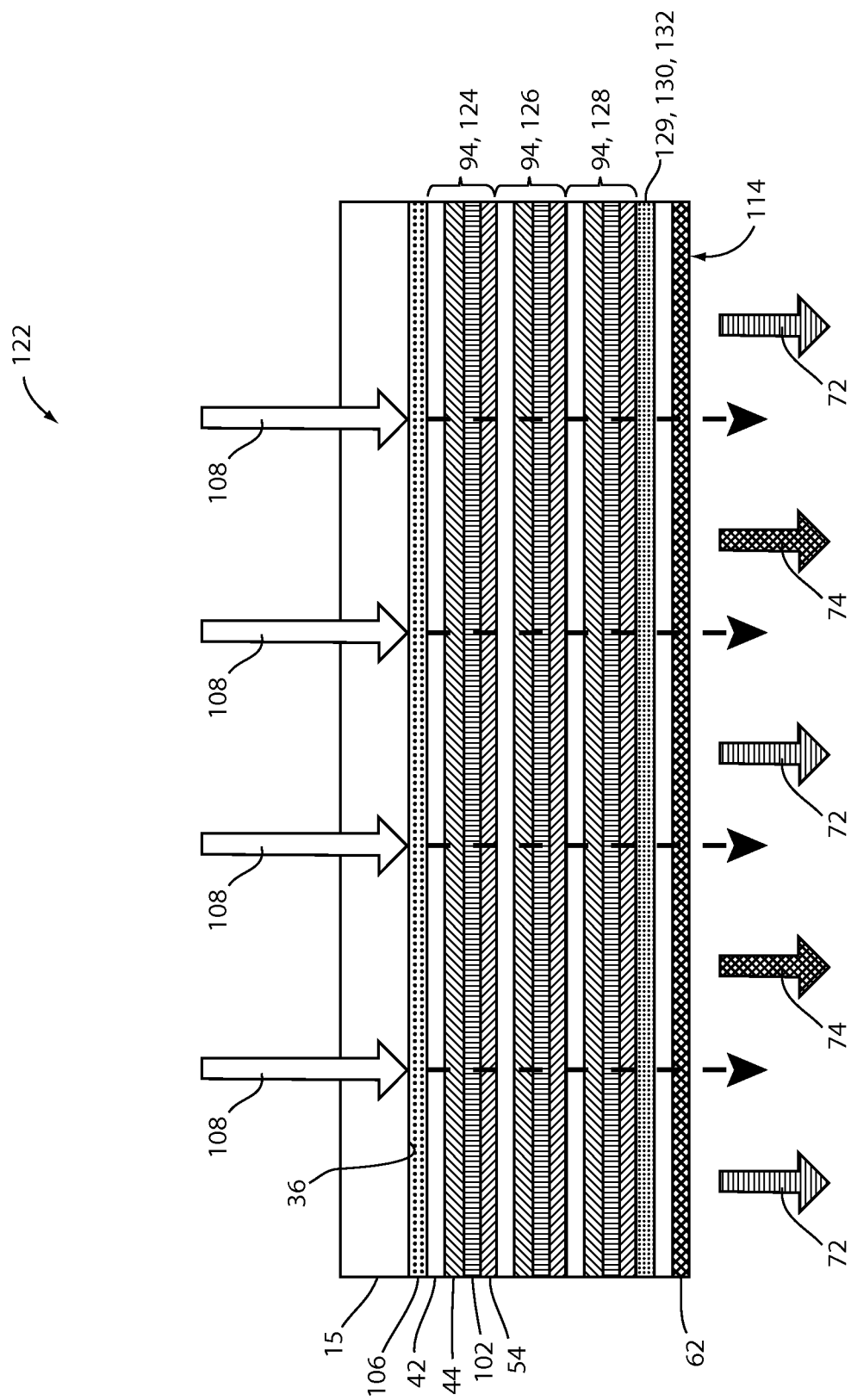
FIG. 5 is a detailed side view of an implementation of an at least semi-transparent color changing surface layer disposed on a glass surface of a vehicle.

For example, as further discussed in reference to FIG. 5, a particular printed LED layer of a stacked emitting layer may be configured to emit a first excitation emission corresponding to a wavelength of light configured to significantly excite a first photoluminescent material. Additionally, at least a second stacked emitting layer may comprise a second photoluminescent material configured to have a substantially different absorption range than the first photoluminescent material. In this configuration, the first excitation emission may excite the first photoluminescent material, while having little to no effect on the second photoluminescent material. Each of the photoluminescent materials may be incorporated in a lighting and/or disinfecting assembly as a combination photoluminescent layer as discussed in FIG. 5 or a plurality of photoluminescent layers as discussed in reference to FIG. 4.

Referring to FIG. 5, a detailed side view illustrating an implementation of a multi-layered lighting assembly 122 is shown disposed on the glass surface 36. The lighting assembly 122 may correspond to the apparatuses 24 and 26 and may be configured to output the unconverted emission 72 and the output emission 74 having a variety of wavelengths of light. Each of a plurality of layers demonstrated in FIG. 5 may correspond to similar layers discussed in reference to FIGS. 2, 3, and 4 have like reference numerals. Specifically, in reference to FIG. 5, the layers form a plurality of stacked emitting layers 94 comprising a first emitting layer 124, a second emitting layer 126, and a third emitting layer 128. In this configuration, the controller 172 may independently activate a printed LED layer 102 of each of the layers 124, 126, and 128 to generate the output emission 74 to illuminate at least a portion of the vehicle 12 in a desired color.

In contrast to the multi-layered lighting assembly 92, the multi-layered lighting assembly 122 comprises a combined photoluminescent layer 130 comprising a plurality of photoluminescent materials. Each of the photoluminescent materials may be configured to have a particular absorption range corresponding to an emission from one of the first emitting layer 124 or the second emitting layer 126. For example, the first emitting layer 124 may be configured to emit a first excitation emission configured to target a first absorption range of the first photoluminescent material 129 incorporated in the combined photoluminescent layer 130. In this way, the first excitation may be configured to excite a first photoluminescent material 129.

The second emitting layer 126 may be configured to emit a second excitation emission configured to target a second absorption range of the second photoluminescent material 132 incorporated in the combined photoluminescent layer 130. The second absorption range may be correspond to a substantially different range of wavelengths of light than the first absorption range. In this way, the second excitation emission may be configured to excite a second photoluminescent material 132 substantially independent of the first photoluminescent material 129. In this configuration, each of the first emitting layer 124 and the second emitting layer 126 may be configured to activate each of the first photoluminescent material 129 and the second photoluminescent material 132 substantially independently.

As described herein, the multi-layered lighting assemblies 92 and 122 may be operable to emit light corresponding to a wide range of colors by selectively activating each of the stacked emitting layers 94 independently to generate the output emission 74 in a wide range of combinations. The first photoluminescent material 129 and the second photoluminescent material 132 may be configured to emit a first color of visible light and a second color of visible light, respectively. For example, the first color may correspond to a substantially green colored light and the second color may correspond to a substantially red colored light. Additionally, the third emitting layer 128 may be configured to emit a blue colored light that may be selectively combined with the red and the green light to control the color of the output emission 74 such that the output emission 74 may appear as any of a variety of colors of light and combinations thereof.

In some embodiments, the first absorption range may correspond to longer wavelengths of light than the second absorption range. In this way, the first photoluminescent material may be illuminated independent of the second photoluminescent material 132. The absorption ranges and resulting emissions may be configured by the particular photoluminescent materials utilized for each of the photoluminescent materials 129 and 132. Various combinations of photoluminescent materials may provide for a wide range of colors and combinations of wavelengths.

The term absorption range as used herein defines a range of wavelengths that excite a photoluminescent material of a photoluminescent layer or combined photoluminescent layer and cause a photoluminescent material to become excited. In response to the excitation, the photoluminescent portion emits an emission having at least one wavelength of light which is at least partially outside the absorption range. In various implementations, the absorption range of the photoluminescent materials as discussed herein may vary. Additionally, the emission of light in the form of emitted fluorescence may be selected based on the material properties of the photoluminescent structures discussed herein.

An example of a particular combination of photoluminescent materials and light sources follows. The particular materials and ranges discussed herein are provided for illustration and not limitation. The first absorption range may correspond to a range of wavelengths in blue and/or near UV range of light having wavelengths of approximately 390-450 nm. The second absorption range may correspond to a substantially non-overlapping range of wavelengths in the UV and/or blue range of light having wavelengths of approximately 250-410 nm. The first excitation emission may be approximately 430 nm and configured to cause the first photoluminescent material 129 to output a green emission of approximately 525 nm. The second excitation emission may be approximately 370 nm and configured to cause the second photoluminescent material 132 to output an orange-red emission of approximately 645 nm. In this way, each of the photoluminescent materials 129 and 132 may be selectively excited by the first emitting layer 124 and the second emitting layer 126 to independently output a substantially green colored light and a substantially orange-red colored light, respectively.

In general, the photoluminescent materials 129 and 132 may be combined in various proportions, types, layers, etc. to generate a variety of colors for the each of the luminescent emissions. Though particular materials and structures of photoluminescent materials are discussed herein, various materials may be utilized without departing from the spirit of the disclosure. In some embodiments, the first photoluminescent material 129 may be configured to have the first absorption range being substantially greater than the second absorption range. Additionally, the second excitation emission may correspond to a substantially shorter wavelength or range of wavelengths than the first excitation emission.

In some implementations, the first photoluminescent material 129 may comprise an organic fluorescent dye configured to convert the first excitation emission of the substantially green colored light. For example, the first photoluminescent material may comprise a photoluminescent structure of rylenes, xanthenes, porphyrins, phthalocyanines, or other materials suited to a particular Stoke shift defined by absorption range and emission fluorescence. The first photoluminescent material 129 may be selected to have a shorter Stoke shift than the second photoluminescent material 132. In this way, each of the photoluminescent materials 129 and 132 may be independently illuminated by the first emitting layer 124 and the second emitting layer 126 to output different colors of light.

The second photoluminescent material 132 may comprise a photoluminescent structure configured to generate a longer stoke shift than the first photoluminescent material 129. The second photoluminescent material 132 may comprise an organic or inorganic material configured to have the second absorption range and a desired output wavelength or color. In an exemplary embodiment, the second photoluminescent material 132 may be of at least one inorganic luminescent material selected from the group of phosphors. The inorganic luminescent material may more particularly be from the group of Ce-doped garnets, such as YAG:Ce. This configuration may provide for a second stoke shift of the second photoluminescent material 132 to be longer than a first stoke shift of the first photoluminescent material 129.

Referring now to FIGS. 4 and 5, additional stacked emitting layers 94 may be incorporated in the multi-layered lighting assemblies 92 and 122. Additionally, one or more of the stacked emitting layers 94 may be omitted from the multi-layered lighting assemblies 92 and 122. For example, a stacked UV emitting layer may be added to or exchanged for one of the stacked emitting layers 94 of the multi-layered lighting assemblies 92 and 122. The stacked UV emitting layer may correspond to the emitting layer 34, as discussed in reference to FIGS. 2 and 3, having the LED sources 48 configured to emit UV light. In this configuration, the controller 172 may be operable to control a color of the output emission 74 as well as emit the unconverted emission 72 as a disinfecting emission into the vehicle 12.

Figure 6:
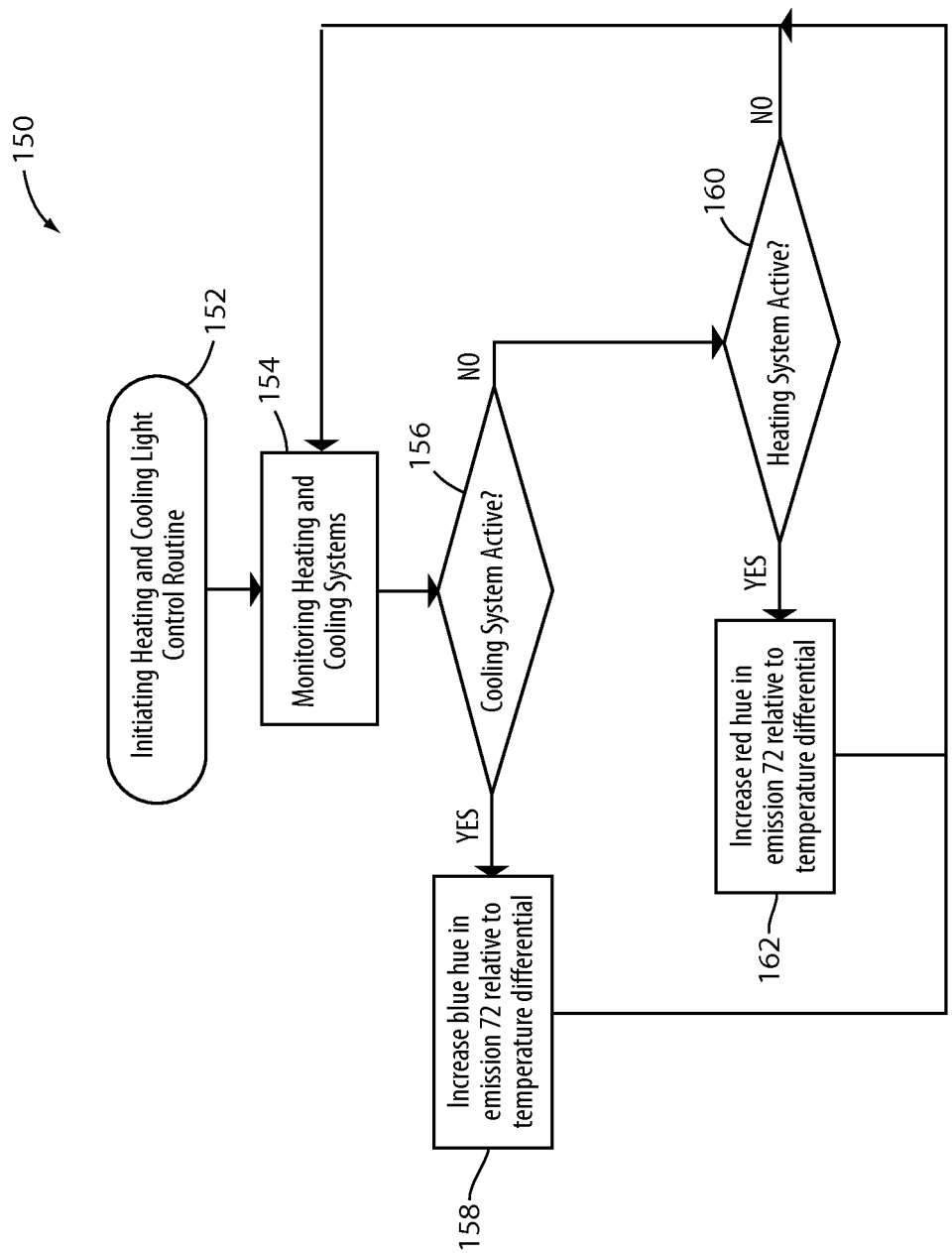
FIG. 6 is a flow chart of a method for controlling the illumination of a light producing assembly.

Referring to FIG. 6, a flow chart of a method 150 for operating the lighting apparatus is shown. The method may relate to a control scheme for a lighting apparatus configured to control a color of the output emission 74. The color of the output emission 74 may be controlled in response to a climate control or temperature control of the vehicle 12. As described herein, the method 150 may provide for the lighting apparatus to illuminate the passenger compartment 10 of the vehicle 12 in a cool or bluish light during a vehicle cooling operation and a warm or reddish light during a vehicle heating operation.

The controller 172 may initiate a heating or cooling light control routine (152) in response to an activation of the vehicle climate control system and/or a lighting apparatus, which may correspond to the lighting apparatus discussed herein. The control routine may begin by monitoring the heating and cooling systems of the vehicle 12 (154). The controller 172 may monitor the heating and cooling systems via the vehicle control system, a communication bus, or various alternative communications received by the vehicle corresponding to various systems of the vehicle 12.

Once activated, the control routine may be processed by the controller 172 to determine if the cooling system is active (156). If the cooling system is active, the controller 172 may increase the blue hue in the output emission 74 relative to the differential between the temperature of the passenger compartment 10 and the temperature setting of the passenger compartment 10 (158). If the vehicle cooling system is determined to be inactive in step 156, the controller 172 may continue the control routine to determine if the heating system is active (160). If the heating system is active as determined in step 160, the controller 172 may increase the red hue in the output emission 74 relative to the differential between the temperature of the passenger compartment 10 and the temperature setting of the passenger compartment 10 (162). Upon identifying the operational status (activity) of the heating and cooling systems of the vehicle 12, the routine 150 may return to step 154 to monitor the heating and cooling systems of the vehicle 12.

Similar to the method 150, the controller 172 may be configured to control the lighting apparatus to emit a color of light corresponding to various vehicle states, signals received from a vehicle bus or any peripheral, or measurement device in communication with the controller 172. For example, the controller 172 may receive a signal based on the vehicle's location from a global positioning (GPS) device and change a color of the output emission 74 in response to the location of the vehicle 12.

Figure 7:
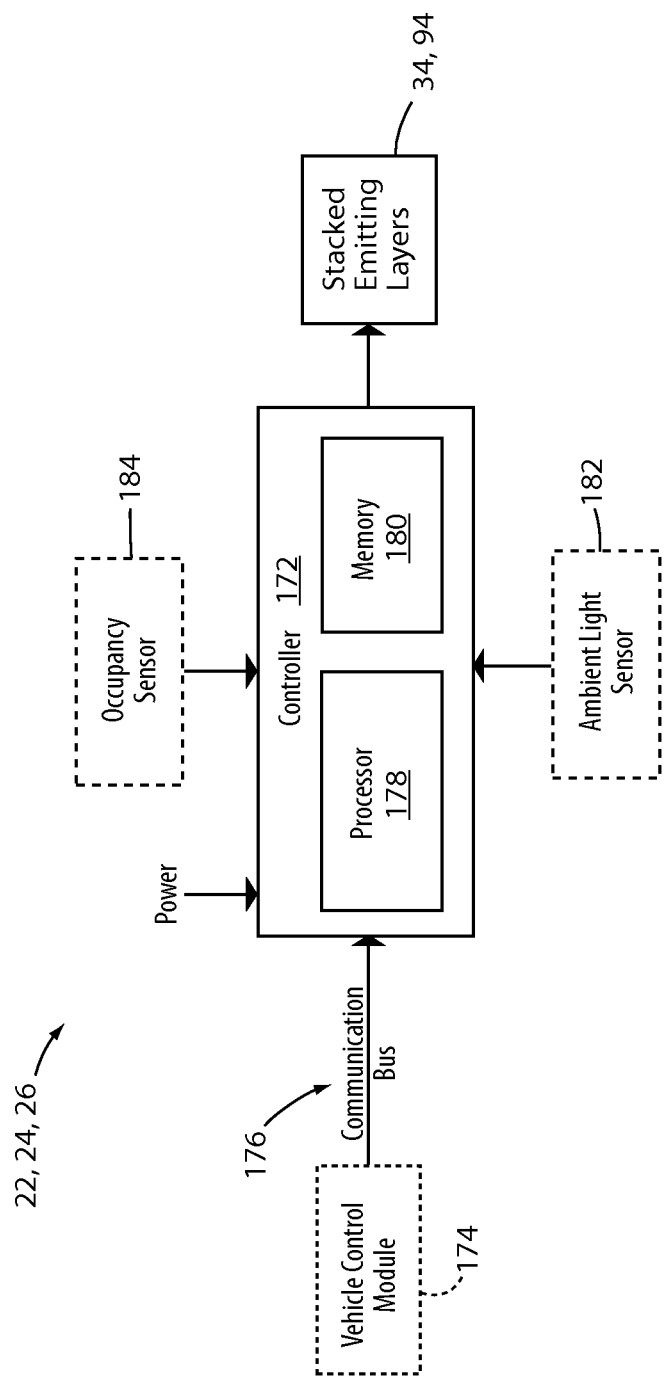
FIG. 7 is a block diagram of a lighting apparatus configured to control the illumination of a light producing assembly.

Referring to FIG. 7, an exemplary block diagram of a system is shown. The system may correspond to the apparatuses 22, 24, and 26 for the vehicle 12. As discussed herein, the controller 172 may be utilized to control various systems similar to those discussed herein including various combinations and variations of such apparatuses. Each of the apparatuses 22, 24, and 26 may comprise the emitting layers 34 and 94. The controller 172 may be in communication with the vehicle control module 174 via a communication bus 176 of the vehicle 12. The communication bus 176 may be configured to deliver signals to the controller 172 identifying various vehicle states. For example, the communication bus 176 may be configured to communicate to the controller 172 a drive selection of the vehicle 12, an ignition state, a door open or ajar status, a remote activation of the LED sources 48, a heating or cooling status of a vehicle heating, cooling, or climate control system, or any other information or control signals that may be utilized to activate or control the emitting layers 34 and 94. Though the controller 172 is discussed herein, in some embodiments, the apparatuses 22, 24, and 26 may be controlled by one or more an electrical or electro-mechanical switches.

The controller 172 may comprise a processor 178 having one or more circuits configured to receive the signals from the communication bus 176 and transmit output signals to control the emitting layers 34 and 94. The processor 178 may be in communication with a memory 180 configured to store instructions to control the activation of the emitting layers 34 and 94. The controller 172 may further be in communication with an ambient light sensor 182. The ambient light sensor 182 may be operable to communicate a light condition, for example a brightness level or intensity of the ambient light proximate the vehicle 12. In response to the level of the ambient light, the controller 172 may be configured to adjust a light intensity output from the emitting layers 34 and 94. The intensity of the light output from the emitting layers 34 and 94 may be adjusted by controlling a duty cycle, current, or voltage supplied to the LED sources 48.

The controller 172 may further be in communication with one or more occupancy sensors 184 configured to detect the presence of a vehicle occupant. An occupancy sensor 184 may generally be configured to detect if a living occupant (e.g. an animal) is inside the vehicle 12. Occupancy sensors 184 may comprise weight sensors in the passenger seats and/or floor, infrared sensors, cameras, microphones, and various proximity sensors that may be configured to detect weight, temperature, motion, sound, etc. in the passenger compartment 10 of the vehicle 12. The controller 172 may utilize signals received from the occupancy sensor 184 to identify whether an occupant is within the interior of the vehicle 12. Upon a determination that the vehicle 12 is unoccupied, the controller 172 may activate the unconverted emission 72 in the form of a disinfecting emission generated by one or more of the emitting layers 34 and 94. In this way, the controller 172 may determine that the vehicle 12 is unoccupied prior to disinfecting the vehicle 12 with the unconverted emission 72 in the form of the disinfecting emission.

In combination with communications received via the communication bus 176, the controller 172 may be operable to identify whether an occupant is within the passenger compartment 10 of the vehicle and additionally whether the interior of the vehicle is secure (e.g. closures and windows of the vehicle are closed). In this configuration, the controller 172 may be configured to control the unconverted emission 72 to be output from the emitting layers 34 and 94 when the vehicle 12 is unoccupied and secure. Additionally, the windows of the vehicle 12 may comprise a UV filtering or blocking coating that may be operable to limit incoming UV radiation from the sun as well as preventing the unconverted emission 72 from escaping the interior of the vehicle 12.

For the purposes of describing and defining the present teachings, it is noted that the terms "substantially" and "approximately" are utilized herein to represent the inherent degree of uncertainty that may be attributed to any quantitative comparison, value, measurement, or other representation. The term "substantially" and "approximately" are also utilized herein to represent the degree by which a quantitative representation may vary from a stated reference without resulting in a change in the basic function of the subject matter at issue.

It is to be understood that variations and modifications can be made on the aforementioned structure without departing from the concepts of the present invention. Though discussed in various illustrative examples in reference to vehicle surfaces, the disinfecting apparatus may be utilized for various surfaces that may correspond to surfaces that are commonly contacted. The surfaces discussed herein may correspond to at least partially transparent surfaces. Such surfaces may include but are not limited to door handles, hand rails, arm rests, head rests, work surfaces (e.g. support surfaces), controls, seats, and a variety of additional fixtures and surfaces that may be contacted throughout ordinary use of the vehicle 12. Further, it is to be understood that the concepts of the present invention are intended to be covered by the following claims unless these claims by their language expressly state otherwise.

What is claimed is:

1. An apparatus configured to disinfect a vehicle comprising:
    a first electrode substantially coating a portion of a partially light transmissive glass panel;
    a plurality of printed LEDs suspended in a semiconductor ink on the first electrode and configured to emit a disinfecting emission;
    a second electrode in electrical connection with the plurality of LEDs; and
    a light transmitting layer forming an interior surface of the glass panel and in connection with the second electrode, wherein the light transmitting layer is operable to transmit at least a portion of the disinfecting emission therethrough such that the portion of the disinfecting emission impinges upon an interior surface of the vehicle.

2. The apparatus according to claim 1, wherein the first electrode and the second electrode correspond to at least partially light transmissive layers.

3. The apparatus according to claim 1, further comprising a controller in communication with the first electrode and the second electrode.

4. The apparatus according to claim 3, wherein the controller is configured to selectively activate the disinfecting emission in response to at least one state of the vehicle.

5. The apparatus according to claim 4, wherein the at least one state corresponds to the vehicle being unoccupied.

6. The apparatus according to claim 3, further comprising at least one occupancy sensor in communication with the controller.

7. The apparatus according to claim 6, wherein the at least one occupancy sensor corresponds to at least one of a seat sensor, a proximity sensor, an infrared sensor, a camera and a microphone.

8. The apparatus according to claim 1, further comprising a photoluminescent layer applied between the second electrode and the light transmitting layer.

9. The apparatus according to claim 8, wherein the photoluminescent layer is configured to convert a portion of the disinfecting emission to an output emission configured to illuminate at least a portion of the vehicle.

10. The apparatus according to claim 9, wherein the disinfecting emission corresponds to a wavelength less than approximately 380 nm and the output emission is greater than approximately 400 nm.

11. A light emitting surface layer for a vehicle comprising:
    a pair of electrodes substantially coating a portion of a glass panel of the vehicle;
    a plurality of printed LEDs in a semiconductor ink disposed between the electrodes and operable to emit an excitation emission of a first wavelength; and
    a photoluminescent layer proximate one of the electrodes configured to convert the excitation emission to an output emission of a second wavelength.

12. The surface layer according to claim 11, wherein the surface layer is connected to an interior surface of the glass panel via an adhesive that is substantially light transmissive.

13. The surface layer according to claim 11, wherein the surface layer is configured to receive light from the glass panel and transmit at least a portion of the light into an interior of the vehicle.

14. The surface layer according to claim 11, further comprising a diffuser film disposed proximate the photoluminescent layer and configured to diffuse the output emission such that the output emission is emitted substantially uniformly from an emitting surface of the surface layer.

15. The surface layer according to claim 11, wherein the surface layer forms a flexible, thin-film layer configured to conform to non-planar surfaces.

16. The surface layer according to claim 11, wherein surface layer has a profile thickness of approximately 0.1 mm to 2 mm.

17. A light emitting assembly for a vehicle comprising:
    a plurality of light generating layers comprising:
        a pair of electrodes substantially coating a portion of a glass panel of the vehicle; and
        a plurality of printed LEDs in a semiconductor ink disposed between the electrodes and operable to emit an excitation emission of a first wavelength, wherein at least one of the light generating layers comprises a photoluminescent layer proximate one of the electrodes configured to convert the excitation emission to at least a first output emission of a second wavelength.

18. The light emitting assembly according to claim 17, wherein each of the light generating layers is configured to generate an output emission corresponding to a different wavelength of light.

19. The light emitting assembly according to claim 18, further comprising a controller configured to selectively activate each of the light generating layers such that a combined output emission corresponds to a variety of the different wavelengths of light.

20. The light emitting assembly according to claim 19, wherein the controller is configured to activate a first light generating layer of the plurality of light generating layers to emit a first color of light in response to a heating operation and activate a second light generating layer of the plurality of light generating layers to emit a second color of light in response to a cooling operation.

* * * * *